United States Patent

Nappa

(10) Patent No.: US 8,058,491 B2
(45) Date of Patent: *Nov. 15, 2011

(54) CATALYTIC ISOMERIZATION BETWEEN E AND Z ISOMERS OF 1,2,3,3,3-PENTAFLUOROPROPENE USING ALUMINUM CATALYST

(75) Inventor: Mario Joseph Nappa, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/674,961

(22) PCT Filed: Aug. 14, 2008

(86) PCT No.: PCT/US2008/073085
§ 371 (c)(1),
(2), (4) Date: Feb. 24, 2010

(87) PCT Pub. No.: WO2009/026080
PCT Pub. Date: Feb. 26, 2009

(65) Prior Publication Data
US 2010/0197979 A1 Aug. 5, 2010

Related U.S. Application Data

(60) Provisional application No. 60/956,185, filed on Aug. 16, 2007.

(51) Int. Cl.
*C07C 17/00* (2006.01)

(52) U.S. Cl. ............................................. 570/236

(58) Field of Classification Search ................... 570/236
See application file for complete search history.

(56) References Cited

U.S. PATENT DOCUMENTS

| | | | | |
|---|---|---|---|---|
| 3,398,204 | A | * | 8/1968 | Gallant ................ 570/236 |
| 3,914,167 | A | * | 10/1975 | Ivy et al. ................ 204/157.98 |
| 5,157,171 | A | | 10/1992 | Sievert et al. |
| 5,162,594 | A | | 11/1992 | Krespan |
| 5,396,000 | A | | 3/1995 | Nappa et al. |
| 5,679,875 | A | | 10/1997 | Aoyama et al. |
| 6,031,141 | A | | 2/2000 | Mallikarjuna et al. |
| 6,369,284 | B1 | | 4/2002 | Nappa et al. |
| 7,709,691 | B2 | * | 5/2010 | Wang et al. ................ 570/236 |
| 2004/0052649 | A1 | | 3/2004 | Murase et al. |

FOREIGN PATENT DOCUMENTS

| | | |
|---|---|---|
| EP | 1918269 A1 | 7/2008 |
| WO | 9403417 A1 | 2/1994 |
| WO | 2004060806 A1 | 7/2004 |
| WO | 2008008351 A | 1/2008 |

OTHER PUBLICATIONS

"Journal of Fluorine Chemistry", Krahl et. al, vol. 127, pp. 663-678, (2006).
"Journal of Fluorine Chemistry", Burton et. al., vol. 44, pp. 167-174, (1989).

* cited by examiner

Primary Examiner — Jafar Parsa

(57) ABSTRACT

A starting material comprising 1,2,3,3,3-pentafluoropropene is contacted with an aluminum chlorofluoride ($AlCl_xF_{3-x}$) catalyst to obtain a final product wherein the Z/E ratio of 1,2,3,3,3-pentafluoropropene is either increased or decreased relative to the Z/E ratio of 1,2,3,3,3-pentafluoropropene in said starting material.

15 Claims, No Drawings

CATALYTIC ISOMERIZATION BETWEEN E AND Z ISOMERS OF 1,2,3,3,3-PENTAFLUOROPROPENE USING ALUMINUM CATALYST

CROSS REFERENCE TO RELATED APPLICATIONS

This application claims the priority benefit of U.S. Provisional Application 60/956,185, filed Aug. 16, 2007.

BACKGROUND

1. Field of the Disclosure

The disclosure herein relates in general to processes for the catalytic isomerization between E and Z isomers of 1,2,3,3,3-pentafluoropropene (HFC-1225ye).

2. Description of Related Art

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

HFC-1225ye, having zero ozone depletion and a low global warming potential, has been identified as a potential refrigerant. HFC-1225ye can also find use in other applications such as solvents, cleaning agents, foam blowing agents, aerosol propellants, heat transfer media, dielectrics, fire extinguishing agents, sterilants and power cycle working fluids. HFC-1225ye may also be used to make polymers. HFC-1225ye may exist as one of two configurational isomers, E or Z, which boil at different temperatures. Depending on the applications, HFC-1225ye may be preferably used as the Z-isomer or the E-isomer or a mixture thereof. It is known that Z-HFC-1225ye is thermodynamically more stable than E-HFC-1225ye.

The liquid phase $SbF_5$ catalyzed isomerization of E-HFC-1225ye to Z-HFC-1225ye has been described by Burton et al. in *Journal of Fluorine Chemistry*, 44, 167-174 (1989). This article shows that the isomerization between E-HFC-1225ye and Z-HFC-1225ye is an equilibrium reaction.

There is a need for new catalytic isomerization processes for the isomerization between E-HFC-1225ye and Z-HFC-1225ye.

SUMMARY

Applicants have found that the Z/E ratio of 1,2,3,3,3-pentafluoropropene can be increased by decreasing the temperature of the HFC-1225ye in presence of an aluminum chlorofluoride ($AlCl_xF_{3-x}$) catalyst, or that the Z/E ratio can be decreased by increasing the temperature of the HFC-1225ye in the presence of an aluminum chlorofluoride catalyst.

Therefore, in accordance with the present invention, a process has been provided to increase the Z/E ratio of 1,2,3,3,3-pentafluoropropene. The process comprises: contacting a starting material comprising 1,2,3,3,3-pentafluoropropene with an aluminum chlorofluoride ($AlCl_xF_{3-x}$) catalyst to obtain a final product, wherein the Z/E ratio of the 1,2,3,3,3-pentafluoropropene in the final product is increased relative to the Z/E ratio of the 1,2,3,3,3-pentafluoropropene in said starting material.

A process has also been provided to decrease the Z/E ratio of 1,2,3,3,3-pentafluoropropene. The process comprises: contacting a starting material comprising 1,2,3,3,3-pentafluoropropene with an aluminum chlorofluoride ($AlCl_xF_{3-x}$) catalyst to obtain a final product, wherein the Z/E ratio of 1,2,3,3,3-pentafluoropropene in the final product is decreased relative to the Z/E ratio of the 2,3,3,3-pentafluoropropene in said starting material.

In either process, the ratio of isomers will depend on the temperature at which the starting material is allowed to equilibrate. Thus, by varying this temperature in the presence of an aluminum chlorofluoride catalyst, applicants have found that the Z/E ratio can be increased or decreased.

The foregoing general description and the following detailed description are exemplary and explanatory only and are not restrictive of the invention, as defined in the appended claims.

DETAILED DESCRIPTION

Before addressing details of embodiments described below, some terms are defined or clarified.

1,2,3,3,3-pentafluoropropene ($CF_3CF=CHF$), also referred to as HFC-1225ye, may exist as one of two configurational isomers, E or Z. HFC-1225ye (with no isomer designation) as used herein refers to either of the isomers, E-1225ye (CAS reg no. 5595-10-8) or Z-1225ye (CAS reg. no. 5528-43-8), as well as any combinations or mixtures of such isomers. HFC-1225ye may be prepared by methods known in the art, such as those described in U.S. Pat. Nos. 5,396,000, 5,679,875, 6,031,141, and 6,369,284.

The term "isomerization process" is intended to mean any process by which the Z/E ratio of HFC-1225ye is changed, either increased or decreased.

The term "Z/E ratio" is intended to mean the molar ratio of Z isomer to E isomer of an olefin. For example, the term "Z/E ratio of HFC-1225ye" is intended to mean the molar ratio of Z-1225ye to E-1225ye.

The term "an elevated temperature" is intended to mean a temperature higher than room temperature.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

The present disclosure provides a process for increasing the Z/E ratio of 1,2,3,3,3-pentafluoropropene. The process comprises comprising: contacting a starting material comprising 1,2,3,3,3-pentafluoropropene with an aluminum chlorofluoride ($AlCl_xF_{3-x}$) catalyst to obtain a final product, wherein the Z/E ratio of the 1,2,3,3,3-pentafluoropropene in the final product is increased relative to the Z/E ratio of the 1,2,3,3,3-pentafluoropropene in said starting material.

In the process for increasing the Z/E ratio of 1,2,3,3,3-pentafluoropropene, the starting material is either E-HFC-1225ye or a mixture of E-HFC-1225ye and Z-HFC-1225ye. The HFC-1225ye in the starting material has a lower Z/E ratio than the HFC-1225ye in the product.

In one embodiment of the process where the Z/E ratio of 1,2,3,3,3-pentafluoropropene is increased, the contacting is conducted at a temperature of from about −20° C. to about 150° C. In another embodiment, the contacting is conducted at a temperature of from about −10° C. to about 100° C. In another embodiment, the contacting is conducted at a temperature of from about 0° C. to about 50° C. In another embodiment, the contacting is conducted at about ambient, i.e., room temperature.

In one embodiment of the process where the Z/E ratio of 1,2,3,3,3-pentafluoropropene is increased, the process occurs in the liquid phase.

The present disclosure also provides a process for decreasing the Z/E ratio of 1,2,3,3,3-pentafluoropropene. The process comprises contacting a starting material comprising 1,2,3,3,3-pentafluoropropene with an aluminum chlorofluoride ($AlCl_xF_{3-x}$) catalyst to obtain a final product wherein the Z/E ratio of 1,2,3,3,3-pentafluoropropene of the final product is decreased relative to the Z/E ratio of 1,2,3,3,3-pentafluoropropene in said starting material.

In this process for decreasing the Z/E ratio of 1,2,3,3,3-pentafluoropropene, the HFC-1225ye in the starting material is either Z-HFC-1225ye or a mixture of E-HFC-1225ye and Z-HFC-1225ye. The HFC-1225ye in the starting material has a higher Z/E ratio than the HFC-1225ye in the product.

In this process for decreasing the Z/E ratio of 1,2,3,3,3-pentafluoropropene, the contacting is conducted at an elevated temperature. In another embodiment, the contacting is conducted at a temperature of from about 300° C. to about 450° C.

In one embodiment of the isomerization process, where the Z/E ratio of 1,2,3,3,3-pentafluoropropene is either increased or decreased, the catalyst may be aluminum chlorofluoride, $AlCl_xF_{3-x}$ (herein after referred to as ACF), wherein x may range from about 0.01 to about 2.99. ACF catalyst may be prepared as described in U.S. Pat. Nos. 5,157,171 or 5,162,594; or in PCT Published Patent Application WO 94/03417, by treatment of $AlCl_3$ with a fluorocarbon such as fluorotrichloromethane (CFC-11) or 1,1,2-trichloro-1,2,2-trifluoroethane (CFC-113).

In either process where the Z/E ratio of 1,2,3,3,3-pentafluoropropene is increased or decreased, the Z/E ratio of 1,2,3,3,3-pentafluoropropene in said product is at least 10. In another embodiment, the Z/E ratio of 1,2,3,3,3-pentafluoropropene in said product is at least 20. In another embodiment, the Z/E ratio of 1,2,3,3,3-pentafluoropropene in said product is at least 40.

In either process where the Z/E ratio of the 1,2,3,3,3-pentafluoropropene is increased or decreased, the contact time for 1,2,3,3,3-pentafluoropropene with the catalyst is not critical. The residence time should be short enough such that reaction of the product with the catalyst does not occur. 1,2,3,3,3-pentafluoropropene product may react with partially fluorinated aluminum chloride (having at least some chlorine remaining) to fully fluorinate the catalyst and produce chlorinated impurities such as HCFC-1224 ($C_3HF_4Cl$).

In either process where the Z/E ratio of the 1,2,3,3,3-pentafluoropropene is increased or decreased, the pressure employed in the isomerization process can be subatmospheric, atmospheric or superatmospheric. In one embodiment of the invention, the isomerization pressure is near atmospheric. In another embodiment of the invention, the isomerization pressure is autogenous.

In certain embodiments of either process where the Z/E ratio of the 1,2,3,3,3-pentafluoropropene is increased or decreased, the contacting may occur in any suitable vapor phase reaction vessel. In one particular embodiment, the reaction vessel may be a tube packed with catalyst through which the gaseous HFC-1225ye may flow.

In certain embodiments of either process where the Z/E ratio of the 1,2,3,3,3-pentafluoropropene is increased or decreased, the reaction vessel for the isomerization process and its associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as nickel-copper alloys commercially available under the trademark Monel®, nickel-based alloys commercially available under the trademark Hastelloy® and nickel-chromium alloys commercially available under the trademark Inconel®, and copper-clad steel.

In either process where the Z/E ratio of the 1,2,3,3,3-pentafluoropropene is increased or decreased, the ratio of isomers will depend on the temperature at which the starting material is allowed to equilibrate. For example, if the E-isomer is desired, and the starting material is the Z-isomer, allowing the starting material to equilibrate at about 350° C. will produce about 10% E-isomer. In an embodiment wherein the starting material is 10% E-isomer and 90% Z-isomer (which is the case when the two isomers are made at about 350° C.) the Z-isomer can be increased to 99% by interconverting them at 25° C. Therefore, the equilibrium composition may be approached from either side.

EXAMPLES

The concepts described herein will be further described in the following examples, which do not limit the scope of the invention described in the claims.

Example 1

Isomerization of E-1225ye to Z-1225ye

Aluminum chlorofluoride ($AlCl_xF_{3-x}$, 1.0 gm) in a dry box was added to a Fisher Porter pressure vessel equipped with a stir bar, pressure gauge, thermocouple, and sample tube, which ended just above the level of the liquid. A mixture of E/Z-1225ye (26% Z) (5.0 gm, 0.038 mol) was transferred into the vessel via vacuum transfer. The mixture was warmed to 16° C. in 8 minutes and a GCMS of gas extracted from above the liquid layer showed 98.8% Z-1225ye and 1.2% E-1225ye. The mixture was held at ambient temperature for about twenty three hours at which time it was observed that some amount of HCFC-1224 ($C_3HClF_4$) was produced from fluorination of the catalyst by the HFC-1225ye.

Example 2

Isomerization of E-1225ye to Z-1225ye

The liquid was allowed to vaporize off of the same catalyst used in Example 1 and a mixture of E/Z-1225ye (26% Z) was transferred into the vessel via vacuum transfer. The mixture was warmed to 0° C. and a GCMS of gas extracted from above the liquid layer showed complete conversion of E-1225ye to Z-1225ye. A sample taken 72 minutes later showed an equilibrium concentration of 1.0% E-1225ye and 98.9% Z-1225ye.

Example 3

Isomerization of E-1225ye to Z-1225ye

Aluminum chlorofluoride ($AlCl_xF_{3-x}$, 0.1 gm) in a dry box was added to a Fisher Porter pressure vessel equipped with a stir bar, pressure gauge, thermocouple, and sample tube, which ended just above the level of the liquid. A mixture of E/Z-1225ye (26% Z) (5.0 gm, 0.038 mol) was transferred into the vessel via vacuum transfer. The mixture was warmed to −1° C. and a sample immediately taken and analyzed by GCMS and it showed 99.1% Z-1225ye and 0.9% E-1225ye.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for increasing the Z/E ratio of 1,2,3,3,3-pentafluoropropene, comprising: contacting a starting material comprising 1,2,3,3,3-pentafluoropropene with an aluminum chlorofluoride catalyst of the formula $AlCl_xF_{3-x}$ wherein x may range from 0.01 to about 2.99 to obtain a final product, wherein the Z/E ratio of the 1,2,3,3,3-pentafluoropropene in the final product is increased relative to the Z/E ratio of the 1,2,3,3,3-pentafluoropropene in said starting material.

2. The process of claim 1 wherein the Z/E ratio of 1,2,3,3,3-pentafluoropropene in said product is at least 10.

3. The process of claim 1 wherein the Z/E ratio of 1,2,3,3,3-pentafluoropropene in said product is at least 20.

4. The process of claim 1 wherein the Z/E ratio of 1,2,3,3,3-pentafluoropropene in said product is at least 40.

5. The process of claim 1 wherein 1,2,3,3,3-pentafluoropropene in said starting material is E-1,2,3,3,3-pentafluoropropene.

6. The process of claim 1 wherein said process occurs in the liquid phase.

7. The process of claim 1 wherein said contact is conducted at a temperature of from about −20° C. to about 150° C.

8. The process of claim 1 wherein said contact is conducted at a temperature of from about −10° C. to about 100° C.

9. The process of claim 1 wherein said contact is conducted at a temperature of from about 0° C. to about 50° C.

10. The process of claim 1 wherein said contact is conducted at about room temperature.

11. A process for decreasing the Z/E ratio of 1,2,3,3,3-pentafluoropropene, comprising: contacting a starting material comprising 1,2,3,3,3-pentafluoropropene with an aluminum chlorofluoride catalyst of the formula $AlCl_xF_{3-x}$ wherein x may range from 0.01 to about 2.99 to obtain a final product, wherein the Z/E ratio of the 1,2,3,3,3-pentafluoropropene in the final product is decreased relative to the Z/E ratio of the 1,2,3,3,3-pentafluoropropene in said starting material.

12. The process of claim 11 wherein 1,2,3,3,3-pentafluoropropene in said starting material is Z-1,2,3,3,3-pentafluoropropene.

13. The process of claim 11 wherein said contact is conducted at an elevated temperature.

14. The process of claim 11 wherein said contact is conducted at a temperature of from about 300° C. to about 450° C.

15. The process of claim 1 or 11, wherein the catalyst is aluminum chlorofloride ($AlCl_xF_{3-x}$).

* * * * *